United States Patent [19]

Mobley et al.

[11] Patent Number: 5,755,234
[45] Date of Patent: *May 26, 1998

[54] PRESSURE-REGULATING EAR PLUG

[75] Inventors: J. Phil Mobley, Canyon Country; Chaoying Zhang, Alhambra; Sigfrid D. Soli, Sierra Madre; Chris Johnson, Irvine, all of Calif.; Drew O'Connell, Cold Spring Harbor, N.Y.

[73] Assignee: House Ear Institute, Los Angeles, Calif.

[*] Notice: The term of this patent shall not extend beyond the expiration date of Pat. No. 5,467,784.

[21] Appl. No.: 560,863

[22] Filed: Nov. 20, 1995

Related U.S. Application Data

[63] Continuation-in-part of Ser. No. 291,165, Aug. 16, 1994, Pat. No. 5,467,784.
[51] Int. Cl.$^6$ .................................................. A61F 11/06
[52] U.S. Cl. .................................... 128/864; 128/867
[58] Field of Search ........................ 128/846, 864–869

[56] References Cited

U.S. PATENT DOCUMENTS 2,437,490  3/1948  Watson et al. ....................... 128/152
3,736,929  6/1973  Mills .................................. 128/151
4,338,929  7/1982  Lundin et al. ....................... 128/864

OTHER PUBLICATIONS

Mossner, W.R., Applications and Properties of Controlled Porosity PM Parts, *Metal Powder Report*, vol. 43, No. 1, Jan. 1988.

Anderson, J.E., Acoustical–Impedance Characteristics of Sintered Stainless Steel, *Journal of The Acoustical Society of America*, vol. 36, No. 5, 811–815, May 1964.

Smugeresky, J.E., et al., Prediction of Gas Permeation From Microstructures of Controlled–Density Sintered Media, *Modern Developments in Powder Metallurgy*, vol. 15 Principles & Processes, 1984 IPMC Proceedings.

Coors Ceramics Company, Porous Ceramics.

*Primary Examiner*—Michael A. Brown
*Attorney, Agent, or Firm*—Blakely, Sokoloff, Taylor & Zafman LLP

[57] ABSTRACT

A pressure regulating ear plug for regulating the rate of change of pressure inside an ear to minimize the pressure differential between the middle ear and a volume of the external ear cavity adjacent the ear drum is made of an ear plug adapted to fit tightly within the external ear cavity with no or minimal air leakage, and disposed within the ear plug is a pressure regulator with a slow leak rate. The pressure regulator is preferably made of a porous ceramic material.

3 Claims, 11 Drawing Sheets

PRESSURE-REGULATING EAR PLUG

This is a continuation-in-part of application Ser. No. 08/291,165 filed Aug. 16, 1994 now U.S. Pat. No. 5,467,784.

BACKGROUND OF THE INVENTION

1. Field of the Invention

The invention relates to a pressure regulating ear plug for controlling the rate of change of pressure in a person's ear which occurs typically during take offs and landings of airplanes, and more specifically, to an ear plug which is designed to lessen the effects of congestion of the Eustachian tube of an airplane passenger, or the like, during a change in altitude.

2. Art Background

Figure 1:
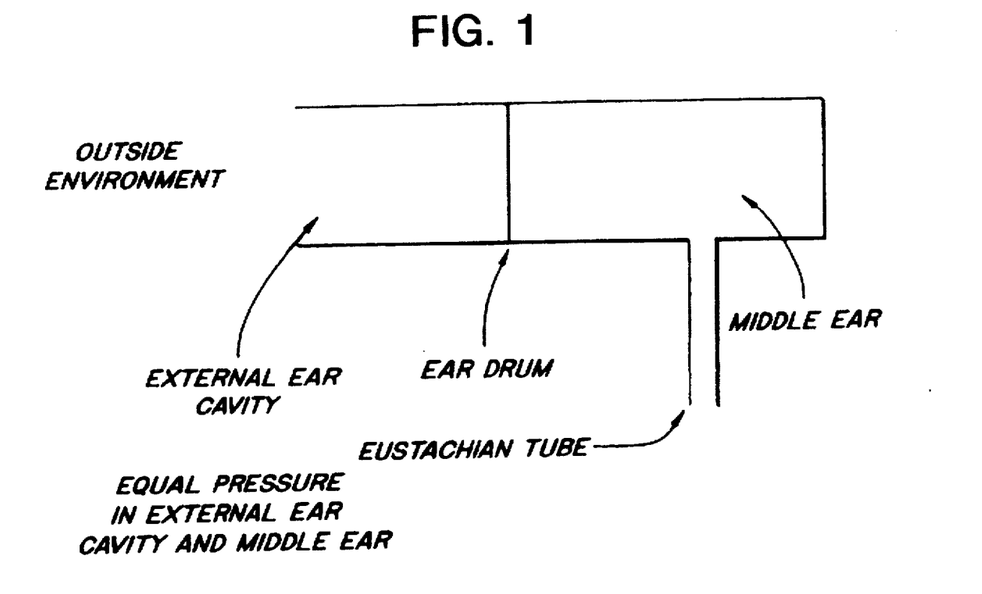
FIG. 1 is a schematic view of an ear in which there is no pressure differential between the external environment and the middle ear.

The middle ear is an air-filled cavity that connects to the outside environment via the Eustachian tube. Under normal conditions, there is no difference between the air pressure in the outside environment and the middle ear. This condition is illustrated in FIG. 1 which is a schematic drawing of the ear, and shows that under normal conditions there is no pressure difference across the eardrum. However, when there is a change in air pressure, such as what an airplane passenger experiences during take-off and landings, there is a difference in the air pressure between the middle ear and the outside environment, the difference in pressure equilibrating over time. Under conditions in which such a pressure differential exists, the Eustachian tube acts as a valve between the outside environment and the middle ear. In this capacity, the Eustachian tube opens for a fraction of a second in response to swallowing or yawning, allowing airflow through it so that the pressure differential between the outside environment and the middle ear equilibrate.

During the ascent of an airplane, the air pressure in the outside environment, that is, the environment inside the airplane and outside the middle ear, is less than that of the pressure inside the middle ear. Under these conditions, the positive relative pressure in the middle ear forces air out of the Eustachian tube thereby lowering the pressure inside the middle ear to the same pressure as the outside environment. If the Eustachian tube is blocked, as described more fully below, the positive pressure in the middle ear applies pressure to the ear drum, as shown schematically in FIG. 2, causing it to bow outward toward the external ear cavity.

Conversely, during the descent of an airplane, the air pressure in the outside environment is greater than that of the pressure inside the middle ear. Under these conditions, the negative relative pressure in the middle ear causes an airflow from the outside environment through the Eustachian tube and into the middle ear, thereby increasing the pressure inside the middle ear to the same pressure as the outside environment. Again, under condition in which the Eustachian tube is blocked, the negative pressure in the middle ear causes deformation of the ear drum, bowing it inward toward the middle ear, as shown schematically in FIG. 3.

Under normal circumstances, when there is no or little blockage of the Eustachian tube, as the pressure differential increases across the ear drum between the middle ear and outside environment, voluntary swallowing and/or chewing releases the pressure through the Eustachian tube.

Figure 2:
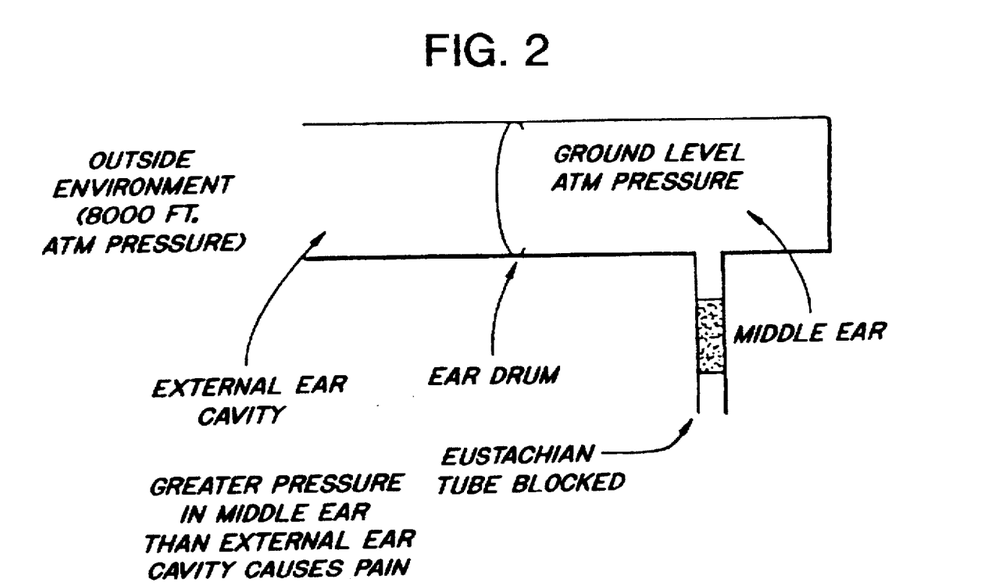
FIG. 2 is a schematic view of an ear in which there is a pressure differential between the external environment and the middle ear wherein the pressure in the middle ear is greater than the pressure in the external environment, and wherein the Eustachian tube is blocked.
Figure 3:
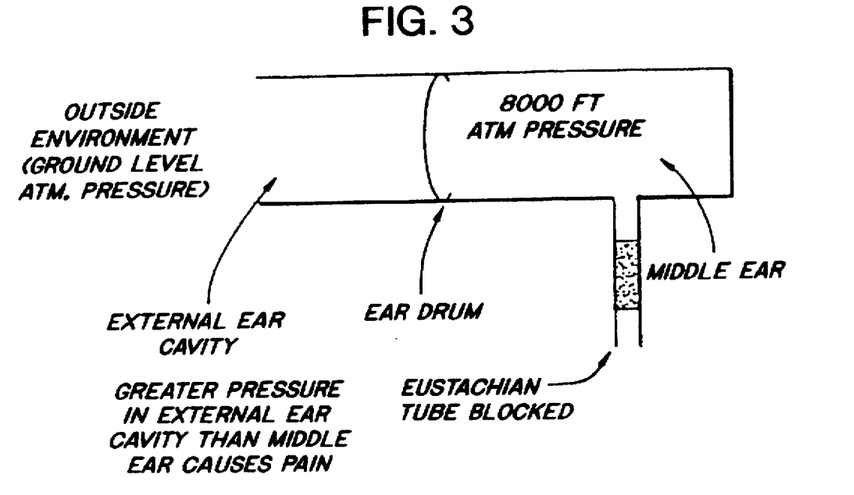
FIG. 3 is a schematic view of an ear in which there is a pressure differential between the external environment and the middle ear wherein the pressure in the middle ear is less than the pressure in the external environment, and wherein the Eustachian tube is blocked.

Individuals sometimes develop colds, or suffer from allergies, respiratory infections, or other medical conditions wherein the Eustachian tubes become swollen thereby partially blocking the airflow through the tubes. In the case of airline passengers and others who are experiencing changes in altitude, the flow of air through the Eustachian tubes is restricted so that a pressure differential between the outside environment and the middle ear may persist for an extended period of time. As indicated above, these pressure differentials are believed to primarily affect the ear drum, causing it to distend, as shown in FIG. 2, or to bow inward toward the middle ear canal, as shown in FIG. 3, depending upon the pressure differential between the middle ear and outside environment. The Eustachian tube blockage prevents the equilibration of the middle ear and outside environment pressures, or delays it. During such pressure differential, as a result of the deformation of the ear drum, there is pain, or at least discomfort to the airplane passenger.

It would thus be desirable to regulate the pressure in the external environment so that the amount of time that the ear drum is deformed is decreased, and the resultant pain is decreased. No one has heretofore attempted to control the pressure differential between the middle ear and the outside environment in order to alleviate the pain caused by such pressure differential as described above.

A number of different types of ear plugs have been designed for the purpose of attenuating sound to protect the user from damage which may be caused by loud noise, music or the like. Some of these plugs are made of silicone and can form an air tight seal in the ear canal. Others are made of a combination open- and closed-cell foam that do not seal the ear canal. A few of these prior art plugs allow rapid equalization of air pressure to reduce discomfort caused by air pressure differences between the ear canal and ambient when the ear plug is inserted into the ear canal, or when the ambient pressure changes. However, none of these plugs are designed to regulate the rate of pressure change in the ear canal, as in the present invention.

U.S. Pat. No. 3,736,929, issued to Allen William Mills ("the '929 patent"), is representative of the prior art which allow rapid equalization of air pressure. The '929 patent discloses an ear plug formed of highly elastic material, with a hollow tube partially occluded with silicone grease, or a rod made of foamed plastic placed along the long axis of the ear plug. The hollow tube or the rod allow rapid pressure equalization across the ear plug. However this device, when used with the silicone grease, is not designed to accommodate the pressure differential caused by an altitude change, because as a result of the geometries of the system as shown, the silicone grease would be ejected from the tube.

U.S. Pat. No. 2,437,490, issued to Norman A. Watson, et al. ("the '490 patent"), is also representative of the prior art. The '490 patent discloses a hollow, elongated plug with an insert that occludes the hollow portion of the plug. The insert is packed with acoustical insulation material which attenuates sound and permits rapid equalization of the air pressure at the opposites ends of the plug.

Thus, it is clear from the foregoing background that none of the prior art ear plug devices are designed or intended to regulate the change in pressure between the middle ear and the external environment, which is the intention and application of the present invention.

SUMMARY OF THE INVENTION

The pressure regulating ear plug of the present invention is designed to make an air tight seal in the external ear canal and to regulate the rate of change in air pressure between the external ear canal and the middle ear when a user is exposed to relatively rapid changes in atmospheric pressure. By so doing, the plug can delay the build-up of an air pressure differential between the external ear canal and the middle ear, which are separated by the ear drum. As a result, the passenger, even with a partially blocked Eustachian tube, has an extended period of time to equalize the pressure differential between the middle ear and the external environment. Normally, these differentials are equalized by the Eustachian tube, which vents the middle ear into the throat. The pressure regulating ear plug creates an enclosed environment between the outside environment and the ear drum. Over time, the pressure regulating ear plug slowly leaks air into or out of the volume immediately exterior to the ear drum, so that the pressure in said volume equilibrates with the pressure outside of the ear plug. This delay increases the time available for the Eustachian tube to perform its function of equilibrating the middle ear pressure with the pressure in the external environment.

A typical example of a situation where the pressure regulating ear plug would be used is during ascent and descent in aircraft. While a person is at ground level the middle ear pressure and the atmospheric pressure are equalized via the Eustachian tube. The Eustachian tube provides a path for the middle ear space to vent to the throat and out to the atmosphere.

When an aircraft is on the ground at the airport, the cabin is open and the cabin is at local atmospheric pressure or in airport jargon, at "altimeter zero." That is, one may be in Denver, in which case you would be 5,000+ feet above sea level, but still at "altimeter zero." During ascent the cabin pressure in the aircraft gradually decreases until it reaches a stable pressure. The absolute cabin pressure stabilizes at an altitude between 8000 and 10,000 feet. While the absolute cabin pressure is dependent upon the type of aircraft, generally for commercial aircraft, the cabin pressure drops to approximately 10.7 to 9.7 pounds per square inch (psi). If the airport is at sea level, where atmospheric pressure is approximately 14.7 psi, this corresponds to a pressure change of 4 to 5 psi.

If the airport is in Denver, where the airport is approximately 5,000 feet above sea level and the local atmospheric pressure is 12.2 psi, this results in a pressure change of only 1.5 to 2.5 psi. If the Eustachian tube is functioning normally, that is, the Eustachian tube allows the middle ear to vent into the throat during chewing, yawning or swallowing, so that air in the middle ear flows out into the throat and the pressure on both sides of the ear drum remains balanced and the traveler experiences minimal discomfort. Generally, chewing, yawning, etc., causes the Eustachian tube to open and equalize the pressure between that of the aircraft cabin and the middle ear. If the Eustachian tube does not open, the pressure in the middle ear will not be released causing the ear drum to be displaced outward toward the external ear canal with gradually increasing discomfort (see FIG. 2). In the case of a descending aircraft, the pressure in the cabin gradually increases from the stable pressure at a nominal altitude of 8,000 feet until it reaches standard atmospheric pressure at the destination airport. During descent the normal Eustachian tube again opens and air flows into the middle ear to balance the pressure across the ear drum. Again, if the Eustachian tube does not open the pressure in the cabin will displace the ear drum inward towards the middle ear with increasing discomfort until it is painful (see FIG. 3). The pressure regulating ear plug controls the rate at which the pressure changes in the external ear canal adjacent the ear drum. The Eustachian tube then has more time to respond to the pressure changes thereby reducing discomfort. The amount of additional time the Eustachian tube has depends on the porosity of the regulating element inside the ear plug.

The ear plug of the present invention is an elongated tube, of the type typically used for sound attenuation, with a slow leak porous medium disposed within the tube. Examples of such porous media include porous metal material and porous ceramic material, and the ceramic material is the presently preferred material for pressure regulation. The ear plug preferably has a leak rate of airflow therethrough in the range of $6.1 \times 10^{-5}$ to $1.4 \times 10^{-4}$ cm$^3$/sec.

It is an object of this invention to regulate the rate of airflow through an ear plug when it forms an air tight pressure seal in the ear canal.

It is a further object of this invention to reduce the rate of pressure change in an external ear canal to reduce the pain and discomfort caused by pressure differences across the ear drum created by the restricted flow of air through the Eustachian tubes. Thus, the system can increase substantially the time required to equalize the pressure in the ear canal to the pressure in the environment in which the user is subjected. The present invention is also effective for the purpose of sound attenuation.

DETAILED DESCRIPTION OF THE INVENTION

Figure 4:
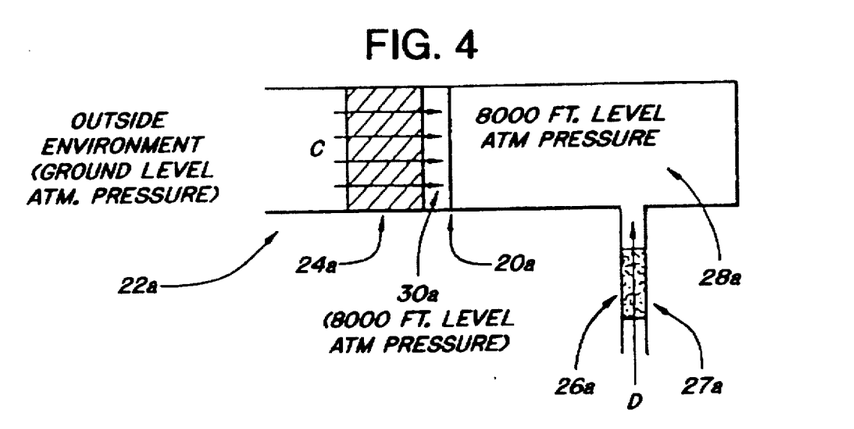
FIG. 4 is a schematic view of an ear in which the regulating ear plug of the present invention is disposed, and in which there is a pressure differential between the external environment and the middle ear, the pressure being less in the middle ear than in the exterior environment, illustrating a descending airplane situation, and wherein the Eustachian tube is blocked.
Figure 5:
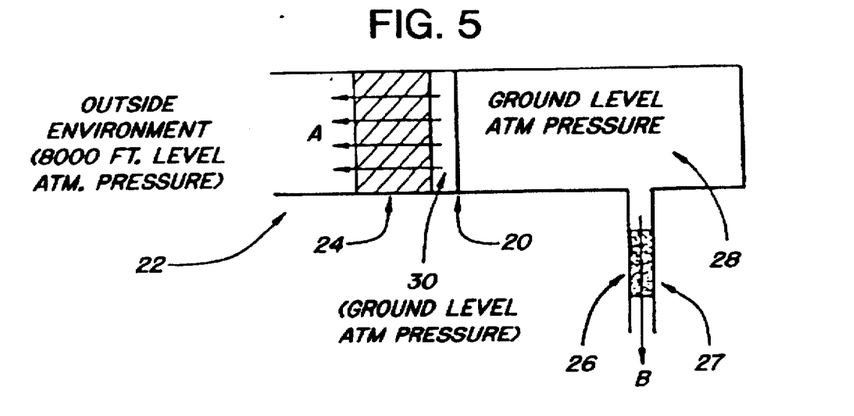
FIG. 5 is a schematic view of an ear in which the regulating ear plug of the present invention is disposed, and in which there is a pressure differential between the external environment and the middle ear, the pressure being greater in the middle ear than in the exterior environment, illustrating an ascending airplane situation, and wherein the Eustachian tube is blocked.

The present invention is illustrated schematically in FIGS. 4 and 5. FIG. 5 is a schematic illustration of the operation of the pressure regulating ear plug of the present invention under conditions comparable to those of FIG. 2, except for the use of the present invention. More specifically, in FIG. 5, which simulates the effect of an ascending airplane, the outside environment has an atmospheric pressure equivalent to an altitude of 8,000 feet, whereas the pressure inside the middle ear 28 is still at ground level atmospheric pressure. The pressure inside the middle ear is a result of the middle ear being pressurized and filled with air at ground level, and not being able to equilibrate to the ambient pressure because the Eustachian tube 26 is blocked, schematically depicted at 27, so that the air in the middle ear 28 cannot escape through the Eustachian tube, or at least not at the desired rate sufficient to cause the desired depressurization of the middle ear. However, because of the installation of the present invention 24, which is schematically depicted in FIGS. 4 and 5, the pressure in the volume between the ear drum 20 and the pressure regulating ear plug 24 remains at ground level atmospheric pressure as well as the pressure in the middle ear. The pressure regulating ear plug is adapted to slowly release air in the volume 30 to the outside environment through the external ear canal 22, and as shown, airflow in direction A illustrated by the arrows occurs. Similarly, provided that there is only partial blockage of the Eustachian tubes, airflow through the blockage 27 travels in the direction depicted by arrow B, so that the pressure in the middle ear equilibrates with the ambient pressure.

Similarly, FIG. 4 is a schematic illustration of the operation of the pressure regulating ear plug of the present invention under conditions comparable to those of FIG. 3, except for the use of the present invention. More specifically, FIG. 4 simulates the effect of a descending airplane. The outside environment has an atmospheric pressure equivalent to an altitude of ground level atmospheric pressure, whereas the pressure inside the middle ear 28a is still at the 8000 foot elevation level atmospheric pressure, which presumably for purposes of this explanation, is the amount of pressure in the aircraft cabin. The pressure inside the middle ear is a result of the middle ear being pressurized and filled with air at the 8000 foot level, and not being able to equilibrate to the ambient pressure because the Eustachian tube 26a is blocked, schematically depicted at 27a, so that the middle ear 28a cannot draw in air through the Eustachian tube, or at least not at the desired rate sufficient to cause the desired pressurization of the middle ear. However, because of the installation of the present invention 24a, the pressure in the volume 30a between the ear drum 20a and the pressure regulating ear plug 24a remains at 8000 foot level pressure which is the same or similar to the pressure in the middle ear. The pressure regulating ear plug is adapted to slowly permit the inflow of air into the volume 30a through the external ear canal 22a and as shown, airflow in direction C illustrated by the arrows occurs. Similarly, provided that there is only partial blockage of the Eustachian tubes, airflow through the blockage 27a travels in the direction depicted by arrow D, so that the pressure in the middle ear equilibrates with the ambient pressure.

Figure 6:
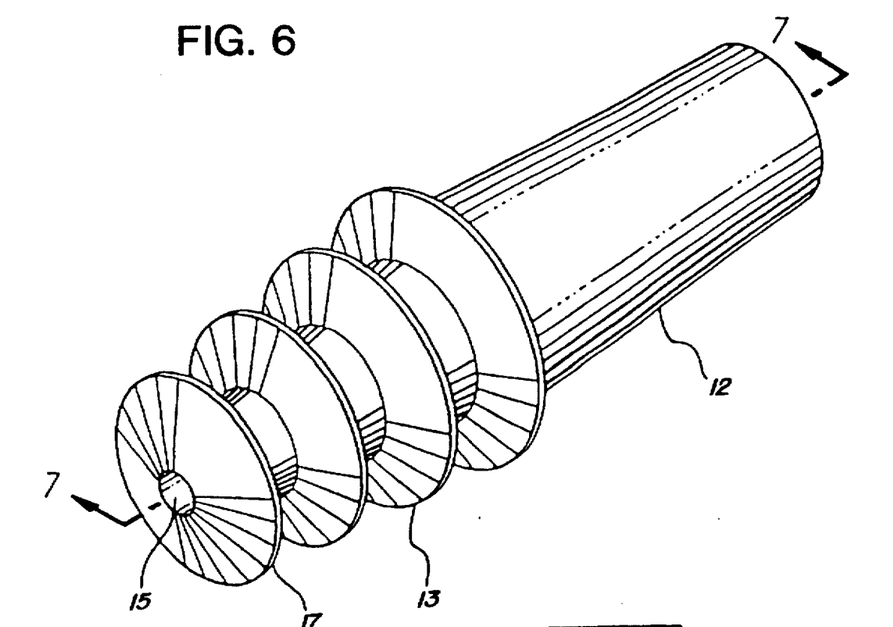
FIG. 6 is a perspective view of the preferred embodiment of the present invention.
Figure 7:
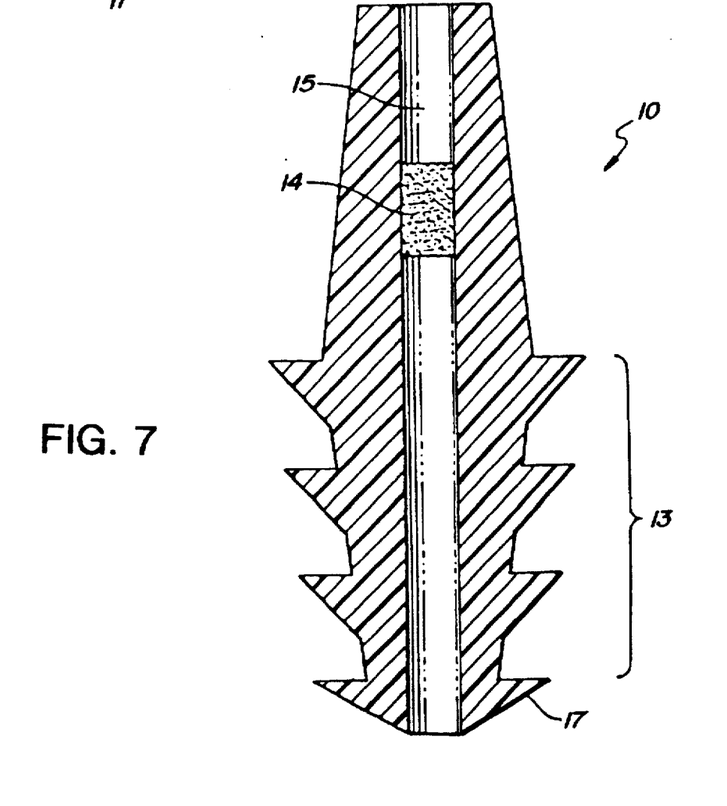
FIG. 7 is a cross-sectional view of the preferred embodiment of the present invention taken through lines 7—7 of FIG. 6.

The preferred embodiment of the invention is illustrated in FIGS. 6 and 7. FIG. 7 shows an enlarged cross-sectional view of the presently preferred embodiment of the pressure equalizing plug 10 of the present invention with each of the components identified. The preferred embodiment has a body 12 shaped generally like a conventional sound attenuating ear plug body comprising a ribbed neck section of the plug 13 which provides an air tight seal with the walls of the ear canal in use. The seal is important to ensure that the pressure regulation is controlled by the pressure regulator 14 and is not affected by a poorly sealed ear plug. There is a bore 15 extending through the plug to permit airflow therethrough. The pressure regulator 14, which is preferably made of porous metal or porous ceramic, and most preferably, porous ceramic material, permits slow air leakage therethrough, preferably in the range of $6.1 \times 10^{-5}$ to $1.4 \times 10^{-4}$ cm$^3$/sec. FIG. 6 shows a perspective view of the subject invention in its preferred embodiment with the plurality of ribs 17 providing a secure and leakage resistant means of retaining the ear plug in the ear and preventing any air leakage except through the porous material.

Figure 8:
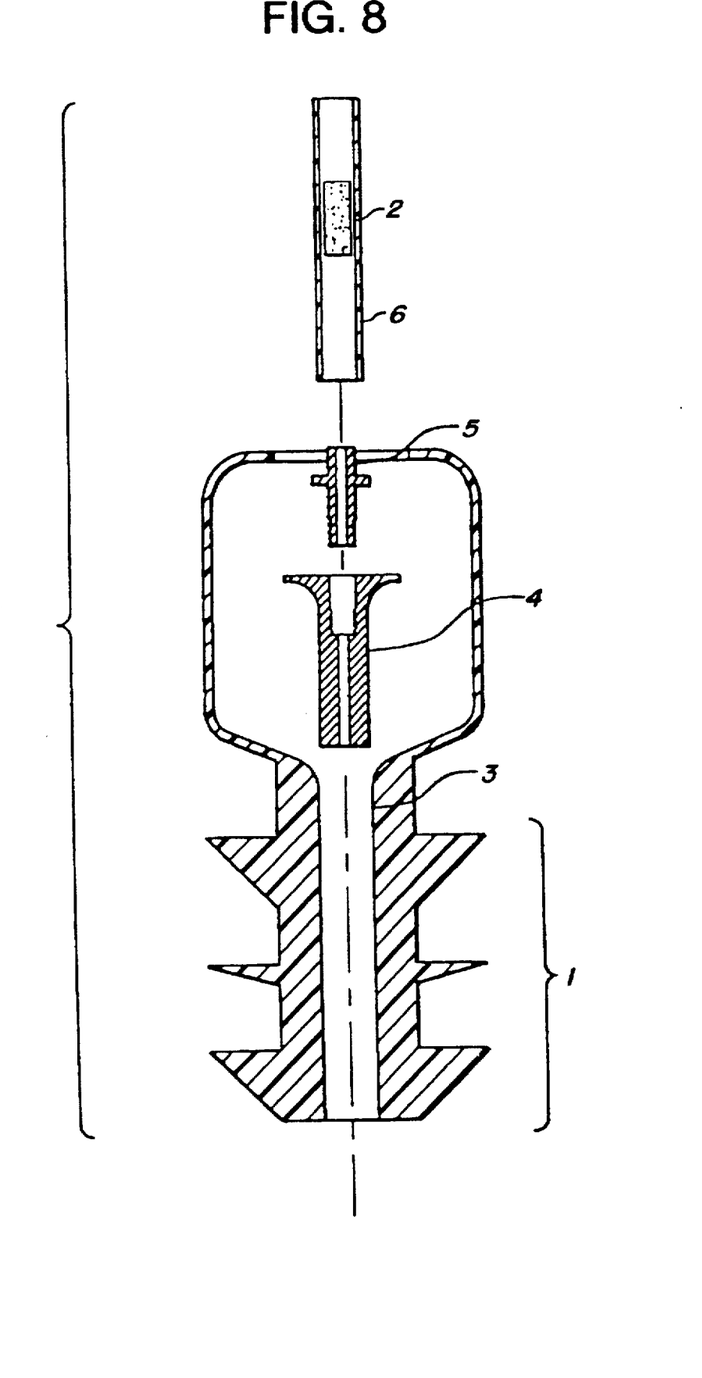
FIG. 8 is an exploded cross-sectional side view of an alternative embodiment of the pressure regulating ear plug of the present invention.

In an alternative embodiment of the present invention, shown in FIG. 8, the pressure regulating ear plug is constructed by drilling a hole 3 through the length of a tight-fitting (air-tight seal is required) conventional sound attenuating protective ear plug body 1 and placing a porous plug 2 inside. A small plastic cone 4 with an internal threaded fitting is inserted into the bore of the ear plug. A tubing adapter 5, threaded on one end with a barbed tube fitting on the other, is screwed into the cone 4. A section of silicone tubing 6 with the porous ceramic air pressure regulator 2 inside is attached to the barbed tube fitting. Depending upon the characteristics of the porous regulator 2, the flow rate or "leak" rate can be modified to control the amount of time it takes to equalize the pressure across the plug. Preferably the flow rate is in the range of $6.1 \times 10^{-5}$ to $1.4 \times 10^{-4}$ cm$^3$/sec.

The porous material must provide a sufficiently slow leak rate in order to ensure that the equilibration time is sufficiently slow to provide adequate protection for the user. In this connection, foam plugs which use open- and closed-cell mixtures were examined for their ability to act as a regulating device, without success, the flow of air through these materials being too great to regulate the pressure across the ear plug.

In the embodiment shown in FIG. 8, the outside diameter of the silicone tubing 6 is about 0.125 inches, and the inside diameter is about 0.078 inches. The outside diameter of the porous regulator 2 is about 0.083 inches so that there is an air tight friction fit between the tubing and the porous regulator 2.

Figure 9:
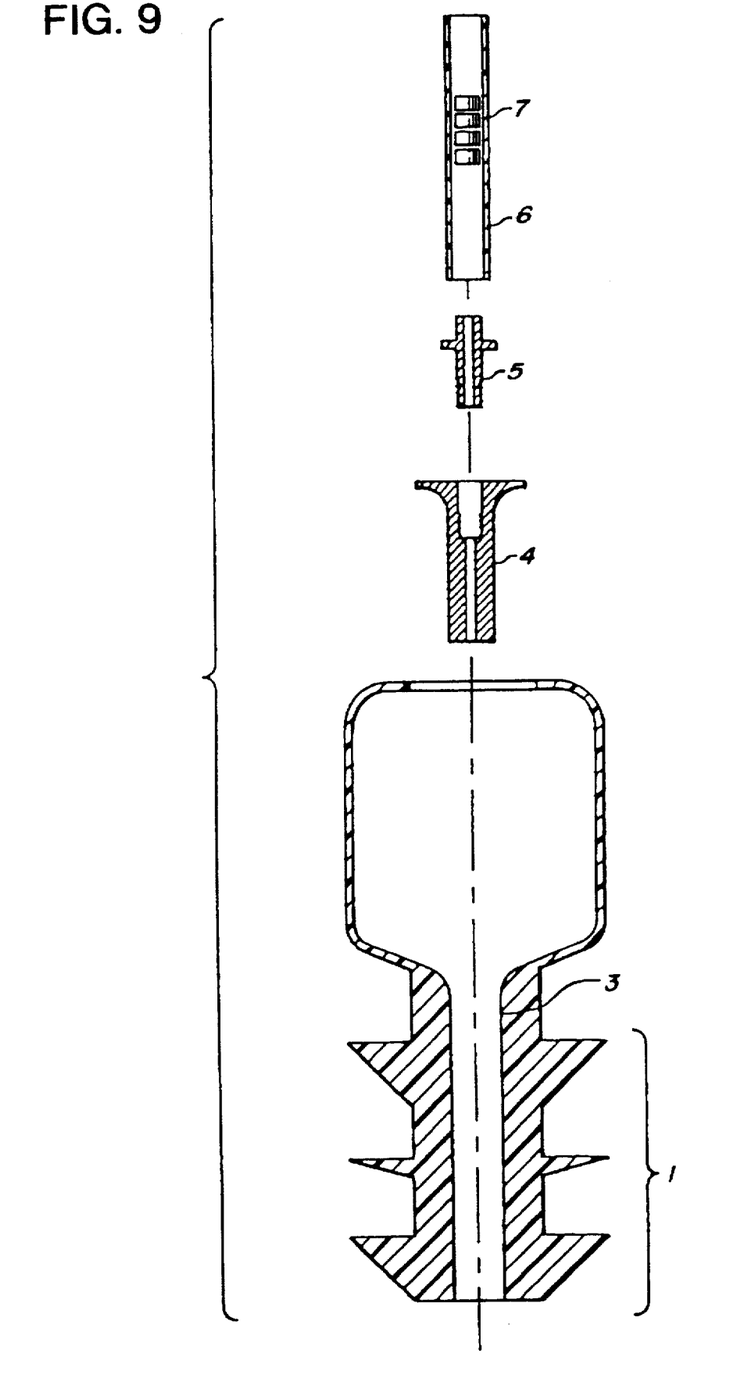
FIG. 9 is an exploded, cross-sectional side view of another alternative embodiment of the pressure regulating ear plug of the present invention.

FIG. 9 depicts another alternative embodiment of the invention. This embodiment has the same basic structure as shown in FIG. 8, except the porous regulator 7 is made from one or more porous metal regulator wafers.

In the presently preferred embodiment, the porous regulator 14 is made from porous ceramic (99% aluminum oxide $Al_2O_3$) and formed into a small right circular cylinder approximately 0.110 inches (2.8 mm) long with a diameter of approximately 0.080 inches (2.0 mm). A free flowing aluminum oxide powder is combined with sintering and compaction aids and loaded into a cylindrical die. The powder is compacted uniaxially by a press to a "green" density and then sintered at high temperature to further partially densify the powder and form a solid porous body. The porosity of the ceramic is controlled by adjusting the particle size, sintering and compaction aids, and controlling the sintering temperature profile. The processed ceramic material preferably has a mean pore size of approximately 2.6 to 3.4 microns. A suitable source for ceramic regulator 14 is Coors Ceramics Company of Golden, Colorado which manufactures the described regulator under product designation AHP-99.

The finished ceramic regulator is forced into the bore of the ear plug 15 which has an inside diameter of approximately 0.072 inches (1.8 mm). The interference fit provides an air-tight seal between the ceramic and the ear plug.

As mentioned above, the ear plug of the present invention has an extremely low leak rate. Rates within the desired range of $6.1 \times 10^{-5}$ to $1.4 \times 10^{-4}$ cm$^3$/sec are difficult to measure accurately with conventional equipment. Accordingly, a special laboratory simulator was constructed in order to achieve an ear plug with the desired leak rate. The simulator consists of two chambers, an inner and an outer chamber. The inner chamber simulates the ear canal, has a volume approximating the volume of the ear canal, and forms an air tight seal around the ear plug so that the air pressure in the inner chamber equilibrates with the air pressure in the outer chamber through the ear plug. The outer chamber fully encloses the inner chamber and is the simulated "cabin" chamber.

Figure 15:
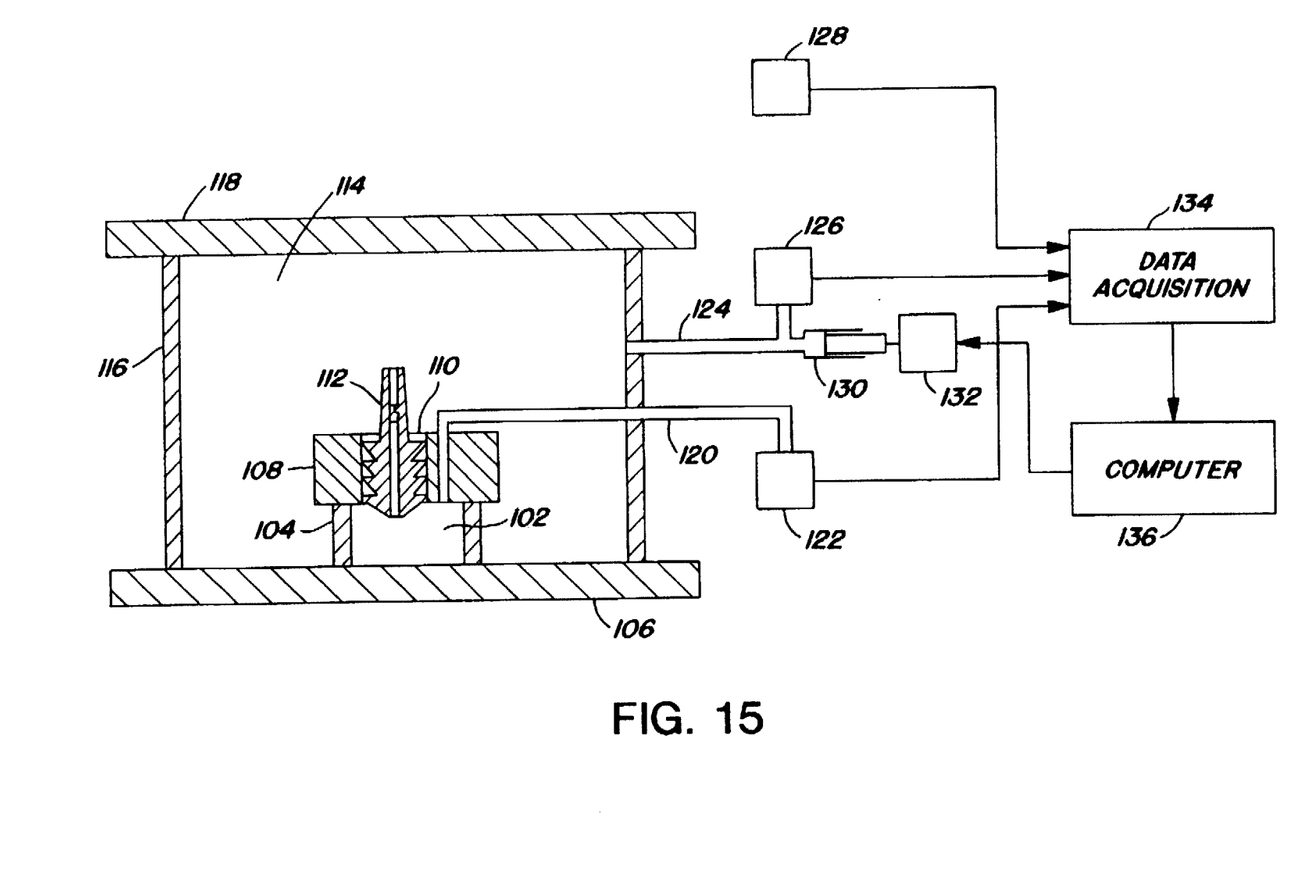
FIG. 15 illustrates a laboratory simulator used to measure the leak rate of ear plugs made in accordance with the present invention.

With reference to FIG. 15, details of the construction of the laboratory simulator will now be described. The inner chamber 102 is an acrylic tube with an inside diameter of approximately 1.3 cm and a height of approximately 0.65 cm, thereby containing a volume approximately equivalent to a typical ear canal. Tube 104 is cemented to acrylic base 106 to achieve an air tight seal. Base 106 comprises an acrylic block approximately 4.5 inches ×3.5 inches ×0.5 inches thick. The top of inner chamber 102 is sealed with another acrylic block 108 approximately 1.5 inches×1.5 inches×0.75 inches thick. Block 108 has an aperture 110 into which the ear plug under test 112 may be inserted.

The outer or "cabin" chamber 114 is defined by a second acrylic tube 116 having an inside diameter of approximately 2.5 inches and a height of approximately 3.0 inches. Outer chamber 114 is sealed at the top with acrylic block 118 approximately 3.5 inches×3.5 inches×0.5 inches thick. During tests, a large clamp (not shown) is placed between blocks 106 and 118 to force block 118 into an air tight seal against outer tube 116.

Tube 120 communicates with inner chamber 102 through block 108 and extends through outer tube 116 where it is coupled to pressure transducer 122. Tube 124 communicates with outer chamber 114 through outer tube 116 and is coupled to pressure transducer 126. Tubes 120 and 124 have outside diameters of approximately 0.125 inches and 0.250 inches, respectively. Pressure transducers 122 and 126 comprise SenSym SCX05-DNC transducers coupled to SenSym SCX-E1 evaluation modules. These sense ±5 psi pressure relative to the ambient air pressure. The transducer outputs are coupled to a data acquisition module 134 such as a Computer Boards CIO-8DAS. A third pressure transducer comprising a SenSym SCX15-ANC transducer with a SenSym SCX-E1 evaluation module is used to sense ambient pressure and is also coupled to the data acquisition module.

Tube 124 from the simulated "cabin" chamber 114 is also coupled via a T-type connector to syringe 130. The syringe allows the chamber to be pressurized or depressurized relative to the ambient pressure. A stepper motor 132, such as a Compumotor Plus, is connected to the syringe plunger handle. The motor speed and direction of rotation are controlled by computer 136. In one direction of rotation, the syringe plunger is pushed in to increase the "cabin" pressure in chamber 114, thereby simulating the cabin pressure change during descent of an aircraft. In the other direction of rotation, the syringe plunger is pulled out to decrease the pressure in chamber 114, thereby simulating the cabin pressure change during ascent of an aircraft.

The laboratory simulator, or an equivalent highly sensitive leak rate measuring device, is essential for selecting an appropriate pressure regulator with the desired leak rate. Although particular preferred embodiments have been described herein, it will be recognized that any stable material having the desired leak rate and dimensions that permit insertion into a human ear could be utilized in the present invention.

EXAMPLE 1

Figure 10:
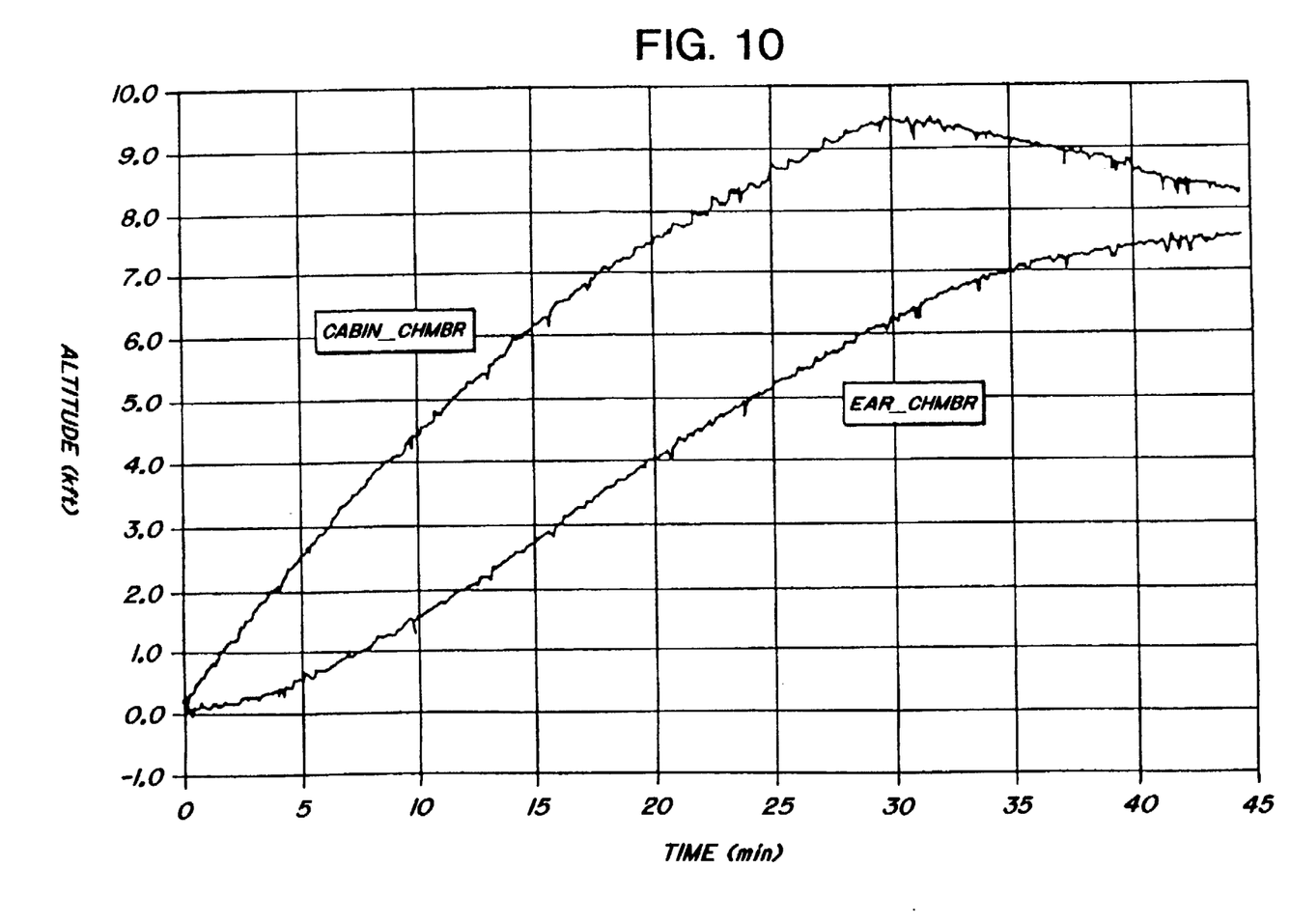
FIG. 10 is a graph showing the operation of an embodiment of the present invention using porous metal as the porous material in the ear plug, during a decrease in pressure as a result of a simulated increase in altitude.
Figure 11:
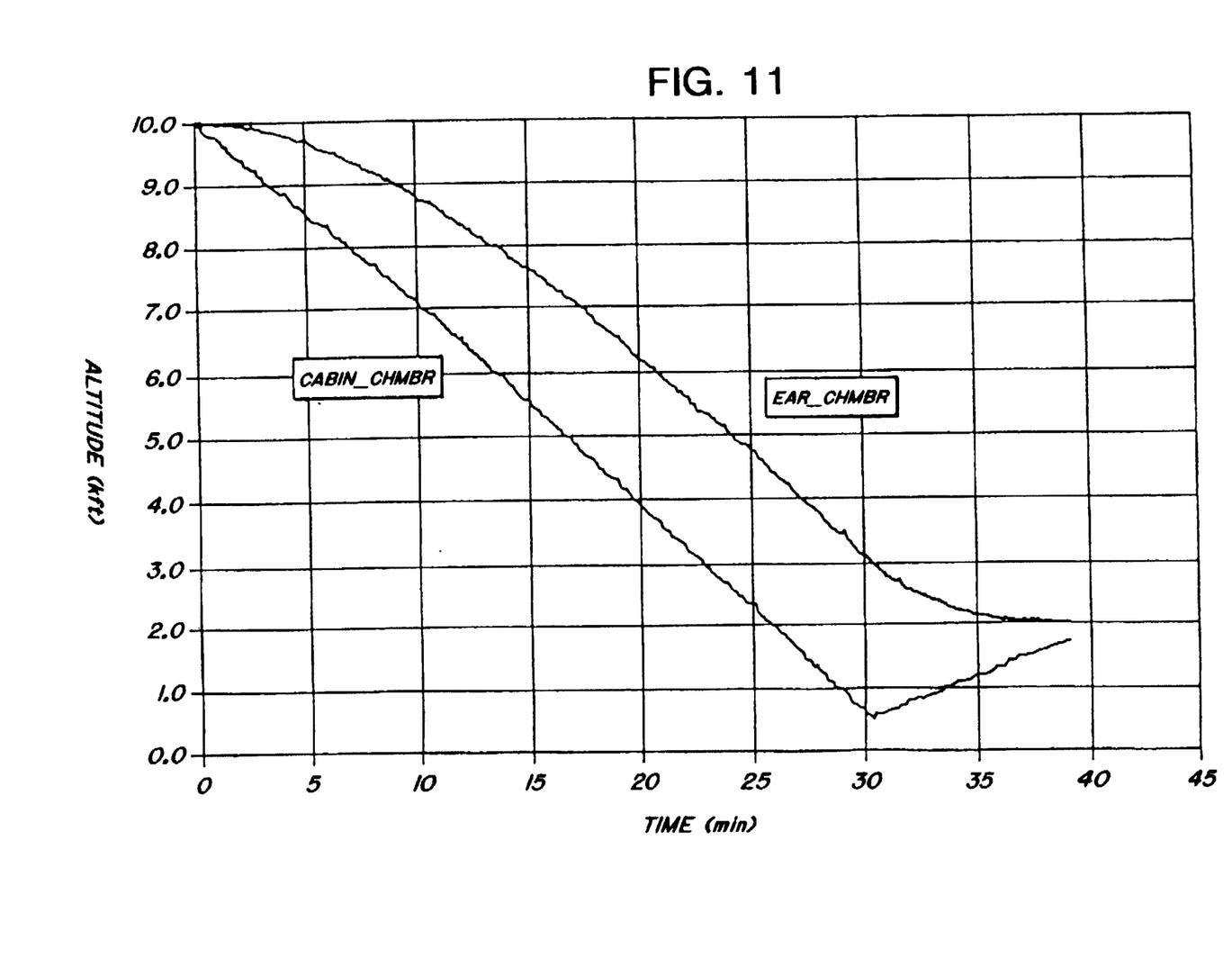
FIG. 11 is a graph showing the operation of an embodiment of the present invention using porous metal as the porous material in the ear plug, during an increase in pressure as a result of a simulated decrease in altitude.

The porous metal regulator ear plug was tested in the laboratory simulator described above. The pressure in the "cabin" chamber was controlled by a computer to simulate an ascent and descent in an aircraft to 10,000 feet. FIGS. 10 and 11 compare the air pressure in the cabin chamber, with the air pressure in the ear chamber. The model makes the assumption that the flight time to reach 10,000 feet is 20 minutes.

The air pressure in the ear chamber lags 10 to 15 minutes behind the air pressure in the cabin chamber on ascent, with the lag time increasing as the cabin air pressure decreases (higher altitudes). Similarly, the air pressure in the ear chamber lags 5 to 10 minutes behind the cabin pressure on descent, with the lag time increasing as the cabin air pressure increases (lower altitudes).

EXAMPLE 2

Figure 12:
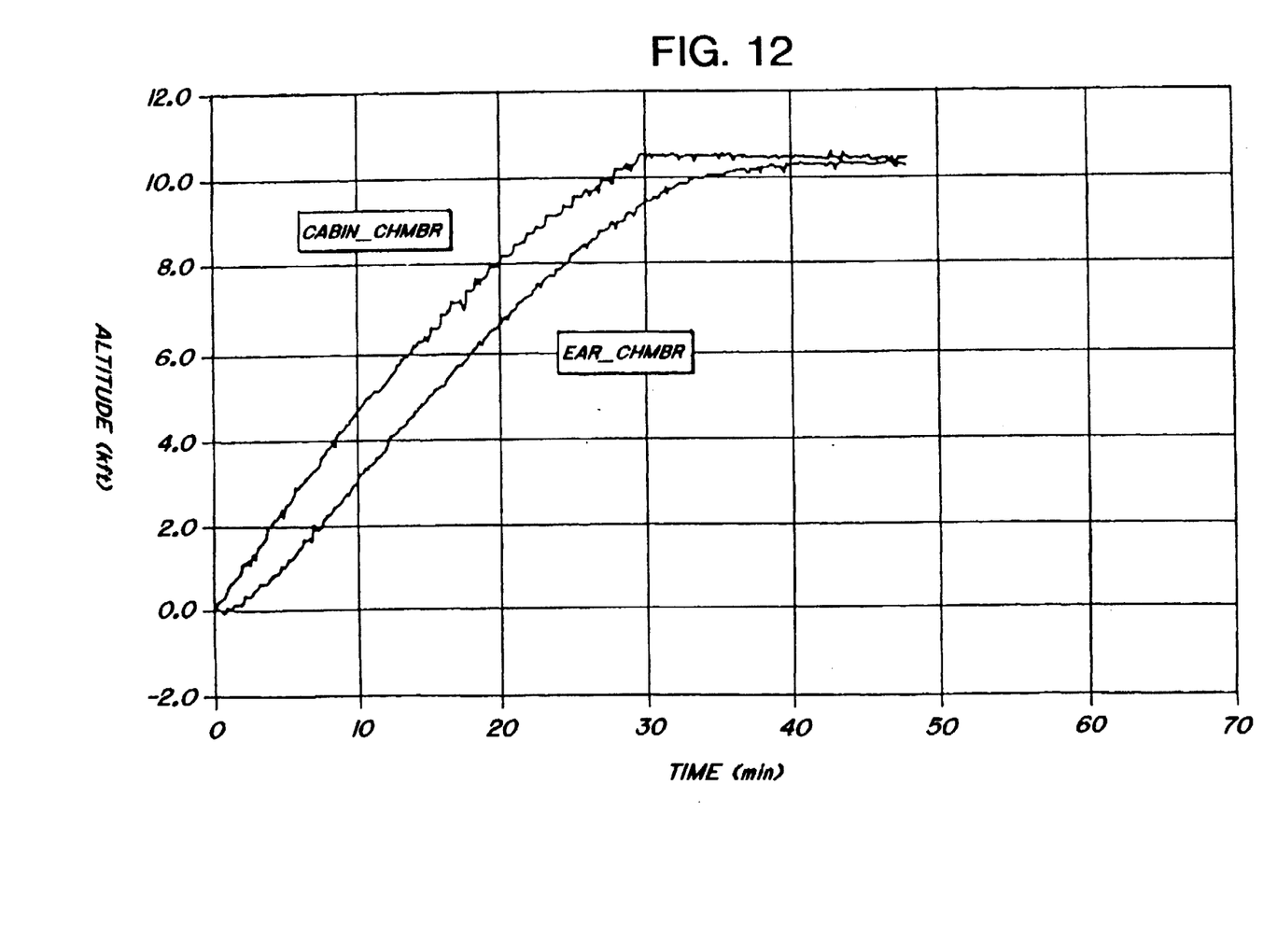
FIG. 12 is a graph showing the operation of an embodiment of the present invention using porous ceramic as the porous material in the ear plug, during a decrease in pressure as a result of a simulated increase in altitude.
Figure 13:
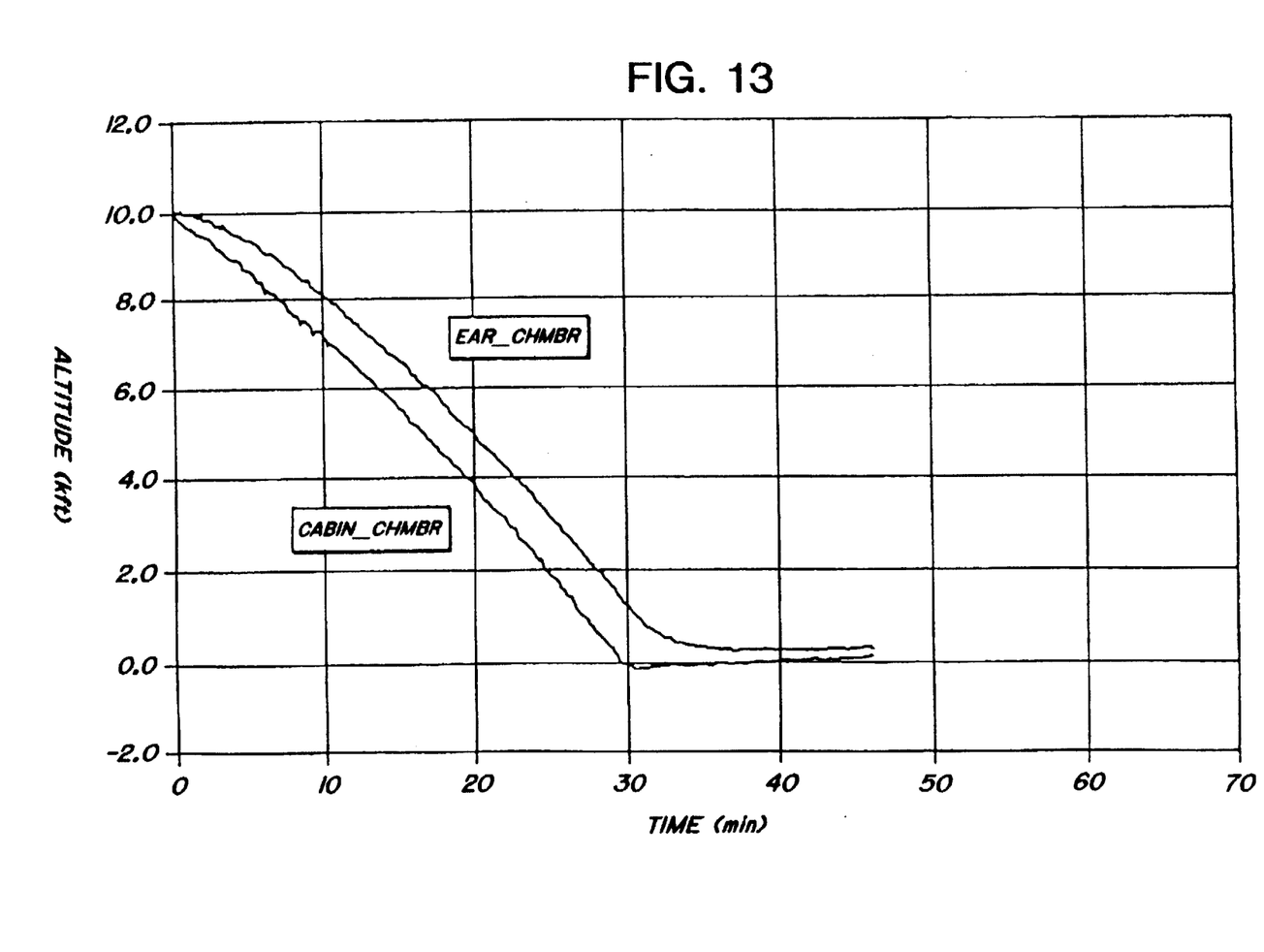
FIG. 13 is a graph showing the operation of an embodiment of the present invention using porous ceramic as the porous material in the ear plug, during an increase in pressure as a result of a simulated decrease in altitude.

The ceramic regulator ear plug was tested in the same simulator, under the same conditions as described in Example 1. The results with the ceramic regulator are shown in FIGS. 12 and 13. With the ceramic regulator the air pressure in the ear chamber lagged 4 to 5 minutes behind the air pressure in the cabin chamber, on ascent and descent.

EXAMPLE 3

The porous ceramic material pressure regulator ear plug was tested with human subjects in an altitude chamber. The porous ceramic air pressure regulator ear plugs were worn by test subjects in one ear with a placebo plug in the other ear. This was a blind test, and neither the subjects nor the experimenters knew which plug was which.

The test evaluated the safety and comfort of the plugs in humans subjected to changes in ambient air pressure. All the test subjects had normal middle ear and Eustachian tube function, and were free of nasal congestion at the time of the test. The test simulated the cabin pressure profile typical for a commercial aircraft, comprising an ascent to 8000 feet in 16 minutes, and then a decent to sea level in 23 minutes. During the test, the test subjects wore both plugs.

The test subjects generally had no difficulty inserting the plugs and maintaining the pressure seal at all times during the simulated flight. Nor did they have any difficulty removing the plug after the simulated flight. All test subjects reported very little difficulty hearing and participating in conversations while wearing the plugs.

The results show that the ear plug can be used to regulate the pressure differential across the eardrum caused by pressure changes during flight.

EXAMPLE 4

Figure 14:
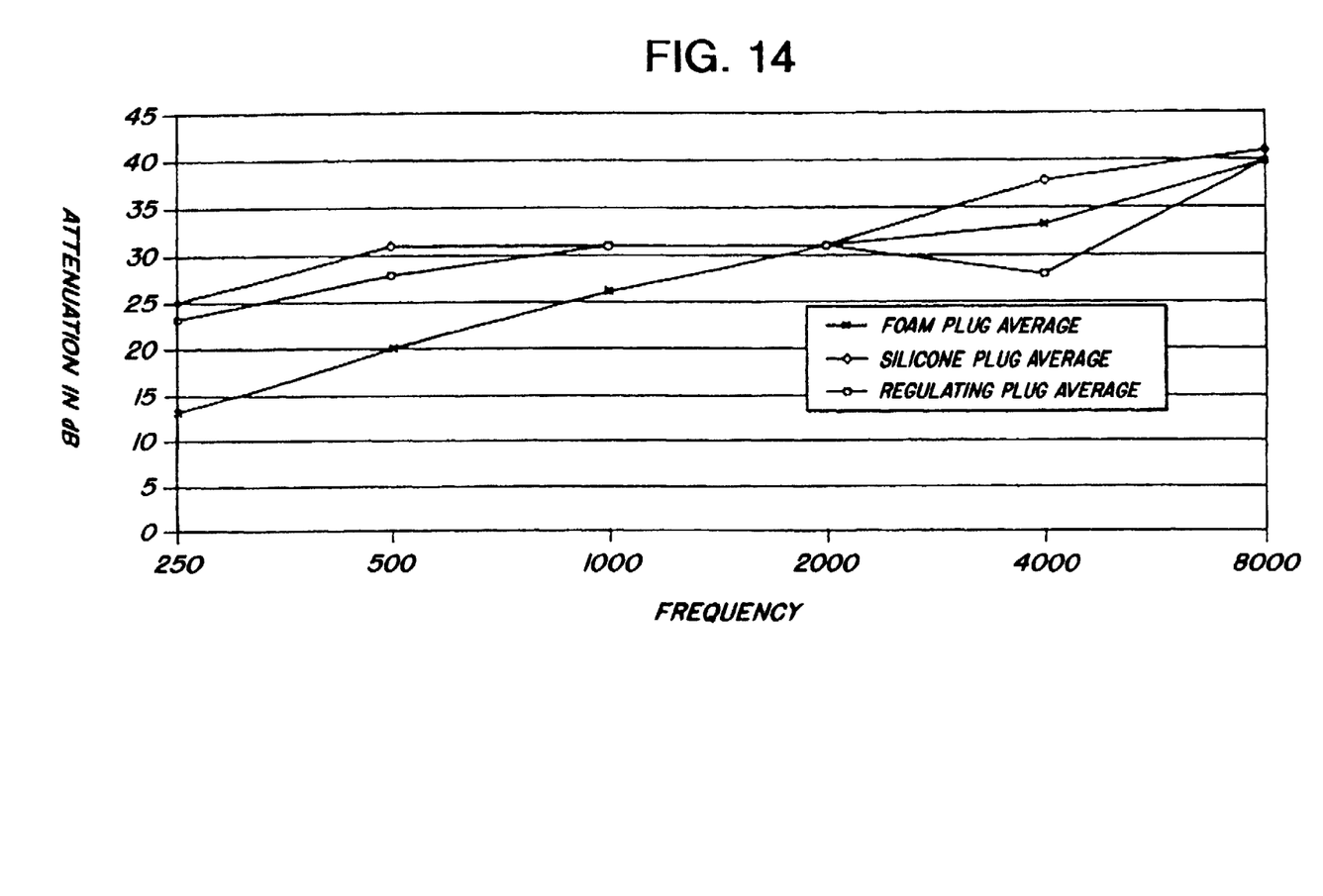
FIG. 14 is a graph showing the results of Example 4 in which 3 ear plugs, including the present invention, referred to as the EarPlane, are tested and compared with respect to the sound attenuation capability.

The configuration of the present invention in which porous ceramic was used as the pressure regulating material was also tested for its capacity to attenuate sound. As shown in FIG. 14, the present invention, which was a porous ceramic material pressure regulating ear plug, and is referred to in the Figure as the Regulating Plug, was compared with two commercially available sound attenuating ear plugs, namely foam plugs and silicone plugs. Tests with several subjects confirmed that throughout a frequency range of 250 to 8000 Hz, the present invention was as effective at attenuating sound as the commercially available ear plugs intended for sound attenuation. Each of the commercially available ear plugs which the present invention was compared against had configurations which were not effective for the purpose of pressure regulation.

It will be obvious to a person of ordinary skill in the art that numerous modifications and changes can be made to the above apparatus in order to accomplish the same function without departing from the spirit and scope of the present invention.

What is claimed is:

1. A method of manufacturing a pressure regulating ear plug comprising the steps of:

forming an ear plug body with a bore therethrough, said ear plug body being adapted to form an airtight seal when inserted into an ear canal;

forming a generally cylindrical ceramic insert by sintering aluminum oxide powder in a press such that the ceramic insert has an airflow rate in an axial direction in the range of $6.1 \times 10^{-5}$ to $1.4 \times 10^{-4}$ cm$^3$/sec;

fitting the ceramic insert within the bore of the ear plug body.

2. The method of claim 1 wherein the step of forming the ceramic insert includes the steps of:

providing a free flowing powder of aluminum oxide;

compacting the powder uniaxially in a press to a first density;

sintering the powder to form a solid porous body.

3. The method of claim 1 further comprising the step of measuring the airflow rate through the ceramic insert in a test fixture to confirm that the airflow rate is within the range of $6.1 \times 10^{-5}$ to $1.4 \times 10^{-4}$ cm$^3$/sec.

* * * * *